United States Patent [19]

Berntsson et al.

[11] 4,045,564

[45] Aug. 30, 1977

[54] BENZIMIDAZOLE DERIVATIVES USEFUL AS GASTRIC ACID SECRETION INHIBITORS

[75] Inventors: Peder Bernhard Berntsson, Molndal; Stig Ake Ingemar Carlsson; Lars Erik Garberg, both of Molnlycke; Ulf Krister Junggren, Pixbo; Sven Erik Sjöstrand, Kungsbacka; Gunhild Wika von Wittken Sundell, Askim, all of Sweden

[73] Assignee: AB Hassle, Goteborg, Sweden

[21] Appl. No.: 655,246

[22] Filed: Feb. 4, 1976

Related U.S. Application Data

[63] Continuation-in-part of Ser. No. 550,637, Feb. 18, 1975, abandoned.

[30] Foreign Application Priority Data

Feb. 18, 1974  Sweden .............................. 7402101

[51] Int. Cl.$^2$ ........................................... A61K 31/415
[52] U.S. Cl. ............................. 424/263; 260/294.8 C
[58] Field of Search ................. 260/294.8 C; 424/263

[56] References Cited

FOREIGN PATENT DOCUMENTS 1,804,450  5/1970  Germany ..................... 260/294.8 C Primary Examiner—Alan L. Rotman
Attorney, Agent, or Firm—Brumbaugh, Graves, Donohue & Raymond

[57] ABSTRACT

Compounds having the structure

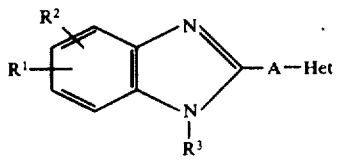

(I)

as well as pharmaceutical compositions containing the same and a method of inhibiting the gastric acid secretion by administering them.

12 Claims, No Drawings

BENZIMIDAZOLE DERIVATIVES USEFUL AS GASTRIC ACID SECRETION INHIBITORS

This application is a continuation-in-part of our copending application Ser. No. 550,637 filed Feb. 18, 1975, now abandoned.

The present invention relates to new compounds having valuable properties in inhibiting gastric acid secretion in mammals, including man, as well as a method of inhibiting gastric acid secretion and pharmaceutical compositions containing said novel compounds.

An object of the present invention is to obtain compounds which inhibit exogenously or endogenously stimulated gastric acid secretion, for treating i.e., peptic ulcer disease.

It has now been found that compounds of the formulas below possess such properties.

Novel compounds of the invention are these of the general formula I

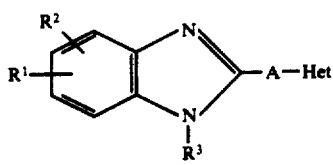

(I)

wherein $R^1$ and $R^2$ are the same or different and are selected from the group consisting of hydrogen, alkyl, halogen, nitro, carboxy, carboalkoxy, carboalkoxyalkyl, hydroxy, alkoxy, hydroxyalkyl and alkanoyl in any position, $R^3$ is selected from the group consisting of hydrogen, alkanoyl, and carboalkoxy, A is selected from the group consisting of —SCH$_2$— and —SCH(CH$_3$)— whereby the S atom is bound to the benzimidazolyl group and Het is selected from the group consisting of 2-pyridyl, and substituted 2-pyridyl, provided that when Het is 2-pyridyl, A is —SCH$_2$—, R and $R^3$ are not both hydrogen, not 5-CH$_3$ and 6-CH$_3$, not hydrogen and 5-NO$_2$, and not hydrogen and 5-Cl, or its therapeutically acceptable salts.

Alkyl $R^1$ and $R^2$ of formula I are alkyl having up to 7 carbon atoms, preferably up to 4 carbon atoms. Thus alkyl R may be methyl, ethyl, n-propyl, isopropyl, n-butyl, isobutyl.

Halogen $R^1$ and $R^2$ are fluoro, iodo, bromo and chloro, preferably bromo and chloro.

Carboxy $R^1$ and $R^2$ are the group HOOC—.

Carboalkoxy $R^1$ and $R^2$ are the groups alkyl—O—OC—, wherein the alkyl group has up to 4 carbon atoms, preferably up to 2 carbon atoms. Carboalkoxy $R^1$ and $R^2$ are e.g. carbomethoxy (CH$_3$OOC—), carboethoxy (C$_2$H$_5$OOC—).

Carboalkoxy alkyl $R^1$ and $R^2$ are the groups alkyl—O—OC—alkyl$^1$—, wherein the alkyl group has up to 4 carbon atoms, preferably up to 2 carbon atoms, and the alkyl$^1$ group has up to 4 carbon atoms, preferably up to 2 carbon atoms, such as carbomethoxymethyl (CH$_3$OOCCH$_2$—) carbomethoxyethyl (CH$_3$OOCC$_2$H$_4$—), carbethoxymethyl (C$_2$H$_5$OOCCH$_2$—) and carbethoxyethyl (C$_2$H$_5$OOCC$_2$H$_4$—).

Alkoxy $R^1$ and $R^2$ are alkoxy groups having up to 5 carbon atoms, preferably up to 3 carbon atoms, such as methoxy, ethoxy, n-propoxy, isopropoxy.

Hydroxyalkyl $R^1$ and $R^2$ have up to 7 carbon atoms, preferably up to 4 carbon atoms and is straight or branched and is e.g., hydroxy methyl, 1-hydroxy-propyl-2, 1-hydroxy-ethyl-2, or 1-hydroxy-2-methyl-propyl-2.

Alkanoyl $R^1$ and $R^2$ have preferably up to 4 carbon atoms and is e.g., formyl, acetyl, or propionyl

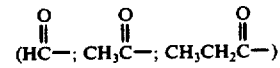

Alkanoyl $R^3$ has preferably up to 4 carbon atoms and is e.g. formyl

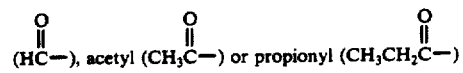

Carboalkoxy $R^3$ is the group alkyl—O—OC—, wherein the alkyl group has up to 4 carbon atoms, preferably up to 2 carbon atoms, and is e.g. carbomethoxy (CH$_3$OOC—) carbethoxy (C$_2$H$_5$OOC—).

The divalent group A can be -thiomethylene, and -thio-(methyl)-methylene.

The heterocyclic group Het which is 2-pyridyl can be further substituted with alkyl or halogen. Such alkyl groups are preferably lower alkyl groups such as methyl, ethyl or propyl. Such halogen substituents are preferably chloro or bromo.

The compounds of the present invention may be prepared according to processes known per se.

Thus, compounds of formula I above may be prepared by reacting compounds of the formula IV

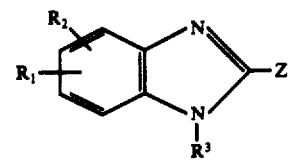

(IV)

wherein $R^1$, $R^2$ and $R^3$ have the same meanings given above and Z is SH, or a reactive esterified hydroxy group, respectively, with a compound of the formula V

Z$^1$CH$_2$Het (V)

wherein Het has the same meaning as given above, and Z$^1$ is a reactive esterified hydroxy group, or SH, respectively, to form a compound of formula I, which compound may be converted to its therapeutically acceptable salts, if so desired.

In the reactions above, Z and Z$^1$ may be a reactive esterified hydroxy group.

A reactive, esterified hydroxy group is particularly a hydroxy group esterified with a strong, inorganic or organic acid, preferably a hydrohalogen acid, such as hydrochloric acid, hydrobromic acid, or hydroiodic acid, further sulphuric acid or a strong organic sulphonic acid such as a strong aromatic acid, e.g., benzenesulphonic acid, 4-bromobenzenesulphonic acid or 4-toluenesulphonic acid. Thus Z and Z$^1$ are preferably chloro, bromo or iodo.

Depending on the process conditions and the starting material the end product is obtained either as a free base or in the form of its acid addition salt, which is included in the scope of the invention. Thus, for example, basic, neutral or mixed salts may be obtained as well as hemiamino, sesqui- or polyhydrates. The acid addition salts of the new compounds may in a manner known per se be transformed into the free base using e.g. basic agents such as an alkali or ion exchanger. On the other hand, the free base obtained may form a salt with an organic or inorganic acid. In the preparation of acid addition salts preferably such acids are used which form suitable therapeutically acceptable salts. Such acids are e.g., hydrohalogen acids, sulphonic acid, phosphoric acid, nitric acid, perchloric acid, aliphatic, alicyclic, aromatic or heterocyclic carboxy or sulphonic acids, such as formic, acetic, propionic, succinic, glycolic, lactic, malic, tartaric, citric, ascorbic, maleic, hydroxymaleic or pyruvic acid, phenylacetic, benzoic, p-aminobenzoic, anthranilic, p-hydroxybenzoic, salicylic or p-aminosalicylic acid, embonic acid, methanesulphonic, ethanesulphonic, hydroxyethanesulphonic, ethylene-sulphonic acids, halogenbenzenesulphonic, toluenesulphonic, naphtylsulphonic acids or sulphanilic acid; methionine, tryptophane, lysine, or arginine.

These or other salts of the new compounds such as e.g., picrates may serve as purifying agents of the free bases obtained. As the free bases are transformed into salts, these are separated and the bases are then set free from the salts again. According to the close relationship between the new compounds in free form and in the form of their salts it will be understood from the above and the following, that, where the context permits, the corresponding salts are also included where the free compounds are mentioned.

Some of the new compounds may, depending on the choice of starting materials and process, be present as optical antipodes or racemate, or if they contain at least two asymmetric carbon atoms, be present as an isomer mixture (racemate mixture).

The isomer mixtures (racemate mixtures) obtained may, depending on physical-chemical differences of the components, be separated into both stereoisomeric (diastereomeric) pure racemates, e.g., by means of chromatography and/or fractional crystallization.

The racemate obtained can be separated according to known methods, e.g., by means of recrystallization from an optically active solvent, by means of microorganisms, or by a reaction with optically active acids forming salts of the compound and separating the salts thus obtained, e.g., by means of their different solubility in the diastereomers, from which the antipodes by the influence of a suitable agent may be set free. Suitably usable optically active acids are, e.g., L- and D-forms of tartaric acid, di-o-tolyltartaric acid, malic acid, mandelic acid, camphorsulphonic acid or china acid. Preferably, the more active part of the two antipodes is isolated.

The starting materials are known or may, if they should be new, be obtained according to processes known per se.

In clinical use the compounds of the invention are administered normally orally, rectally or by injection in the form of a pharmaceutical preparation, which contains an active component either as a free base or as pharmaceutically acceptable, non-toxic acid addition salt, e.g., the hydrochloride, lactate, acetate, sulphamate or the like in combination with a pharmaceutically acceptable carrier. Where a new comound of the invention is mentioned either the free amine base or the acid addition salt of the free base is also intended, even if the compounds are generally or specifically described, provided that the context in which such expressions are used, e.g., in the examples, permits. The carrier may be a solid, semisolid or liquid diluent or a capsule. The pharmaceutical preparations are a further object of the invention. Usually the amount of active compound is between 0.1 to 95% by weight of the preparation, suitably between 0.5 to 20% by weight in preparations for injection and between 2 and 50% by weight in preparations for oral administration.

In the preparation of pharmaceutical compositions containing a compound of the present invention in the form of dosage units for oral administration the compound elected may be mixed with a solid, pulverulent carrier, such as, e.g., with lactose, saccharose, sorbitol, mannitol, starch, as potato starch, corn starch, amylopectin, cellulose derivatives or gelatine, as well as with an antifriction agent such as magnesium stearate, calcium stearate, polyethyleneglycol waxes or the like, and be pressed into tablets. If coated tablets are desired, the above prepared core may be coated with a concentrated solution of sugar, which solution may contain e.g., gum arabicum, gelatine, talc, titaniumdioxide or the like. Furthermore, the tablets may be coated with a lacquer dissolved in an easily volatile organic solvent or mixture of solvents. To this coating a dye may be added in order easily to distinguish between tablets with different active compounds or with different amounts of the active compound present.

In the preparation of soft gelatine capsules (pearl-shaped, closed capsules), which consist of gelatine and e.g. glycerine or in the preparation of similar closed capsules the active compound is mixed with a vegetable oil. Hard gelatine capsules may contain granules of the active compound in combination with a solid, pulverulent carrier such as lactose, saccharose, sorbitol, mannitol, starch (e.g. potato starch, corn starch or amylopectin), cellulose derivatives or gelatine.

Dosage units for rectal administration may be prepared in the form of suppositories, which contain the active substance in a mixture with a neutral fat base, or they may be prepared in the form of gelatin-rectal capsules which contain the active substance in a mixture with a vegetable oil or paraffin oil.

Liquid preparations for oral administration may be present in the form of syrups or suspensions, e.g. solutions containing from about 0.2% by weight to about 20% by weight of the active substance described, wherein the remainder consists of sugar and a mixture of ethanol, water, glycerol and propylene glycol. If desired, such liquid preparations may contain coloring agents, flavoring agents, saccharine and carboxymethylcellulose as a thickening agent.

Solutions for parenteral administration by injection may be prepared as an aqueous solution of a water soluble pharmaceutically acceptable salt of the active compound, preferably in a concentration from about 0.5% by weight to about 10% by weight. These solutions may also contain stabilizing agents and/or buffering agents and may suitably be available in different dosage unit ampoules.

The preparation of the pharmaceutical tablets for peroral use is carried out in accordance with the following method:

The solid substances included are ground or sieved to a certain particle size. The binding agent is homogenized and suspended in a certain amount of solvent. The therapeutic compound and necessary auxiliary agents are mixed with continuous and constant mixing with the binding agent solution and are moistened so that the solution is uniformly divided in the mass without over-moistening any parts. The amount of solvent is usually so adapted that the mass attains a consistency similar to wet snow. The moistening of the pulverulent mixture with the binding agent solution causes the particles to gather together slightly into aggregates and the real granulating process is carried out in such a way that the mass is pressed through a sieve in the form of a net of stainless steel having a mesh size of about 1 mm. The mass is then placed in thin layers on a tray to be dried in a drying cabinet. This drying takes place during 10 hours and has to be standardized carefully since degree of dampness of granulate is of utmost importance for the following process and for the characteristics of the tablets. Drying in a fluid bed may possibly be used. In this case, the mass is not put on a tray but is poured into a container having a net bottom.

After the drying step the granules are sieved so that the desired particle size is obtained. Under certain circumstances powder is removed.

To the so-called final mixture, disintegrating, antifriction agents and antiadhesive agents are added. After this mixture is made the mass should have its correct composition for the tableting step.

The cleaned tablet punching machine is provided with a certain set of punches and dies, whereupon the suitable adjustment for the weight of the tablets and the degree of compression is tested out. The weight of the tablet determines the size of the dose in each tablet and is calculated starting from the amount of therapeutic agent in the granules. The degree of compression affects the size of the tablet, its strength and its ability to disintegrate in water. Especially as regards the two latter properties the choice of compression pressure (0.5 to 5 ton) involves a balancing condition. When the correct adjustment is set, the preparation of tablets is started, which is carried out at a rate of 20,000 to 200,000 tablets per hour. The pressing of the tablets requires different times and depends on the size of the batch.

the tablets are freed from adhering powder in a specific apparatus and are then stored in closed packages until they are delivered.

Many tablets, especially those which are rough or bitter, are coated with a coating of a layer of sugar or some other suitable material.

The tablets are usually packed by machines having an electronic counting device. The different types of packages consist of glass or plastic gallipots, but also boxes, tubes and specific dosage adapted packages are suitable.

The daily dose of the active substance varies and depends on the type of administration, but as a general rule it is 100 to 400 mg/day of active substance for peroral administration and 5 to 20 mg/day for intravenous administration.

The following illustrates the principle and the adaption of the invention without, however, being limited thereto. Temperature is given in degree Celsius.

The starting materials in the examples presented below were prepared in accordance with the following:

A 1,2-diamino compound, as o-phenylenediamine was reacted with potassium ethylxanthate (according to Org. Synth. vol. 30 p. 56) to form a 2-mercaptobenzimidazole.

2-Chloromethylpyridine was prepared by reacting 2-hydroxy-methylpyridine with thionylchloride (according to Arch. Pharm. vol. 26 pp. 448-451 (1956)).

2-Chloromethylbenzimidazole was prepared by condensating o-phenylenediamine with chloroacetic acid.

EXAMPLE 1

0.1 moles of 4-methyl-2-mercaptobenzimidazole were dissolved in 20 ml of water and 200 ml of ethanol containing 0.2 moles of sodium hydroxide. 0.1 moles of 2-chloromethylpyridine hydrochloride were added and the mixture was refluxed during 2 hours. The sodium chloride formed was filtered off and the solution was evaporated in vacuo. The residue was dissolved in acetone and was treated with activated carbon. An equivalent amount of concentrated hydrochloric acid was added, whereupon the monohydrochloride of [2-pyridylmethylthio]-4-methyl-2-benzimidazole was isolated. Yield 0.05 moles melting point 137° C.

EXAMPLES 2-17

The preparation was carried out in accordance with Example 1 above. The compounds prepared are listed in the following table 1.

EXAMPLE 18

13.5 g (0.05 moles) of 2-[2-pyridylmethylthio]-benzimidazole hydrochloride, 3.9 g (0.05 moles) of acetylchloride, and 10.1 g (0.1 moles) of triethylamine were dissolved in 100 ml of acetonitrile. The mixture was heated in a 40° C-waterbath for 30 min. After cooling the crystals formed were filtered off which were suspended in water in order to dissolve the triethylamine hydrochloride. The residue, 2-[2-pyridylmethylthio]-N-acetylbenzimidazole, was filtered off. Yield 7.2 g (51%) M.p. 119°-124° C as base.

EXAMPLE 19

2-[2-pyridylmethylthio]-N-methoxycarbonylbenzimidazole was prepared in accordance with Example 18 above.

Table I

Compounds of formula I prepared

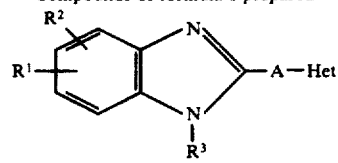

| Ex. | R² | R¹ | R³ | A | Het | M.P. ° C | |
|-----|------|--------|---|--------|----------|---------|----------|
| 1 | H | 4-CH₃ | H | —SCH₂— | 2-pyridyl | 137-83 | (2 · HCl) |
| 2 | 6-CH₃ | 4-CH₃ | H | —SCH₂— | 2-pyridyl | 230 | (HCl) |
| 3 | H | 5-C₂H₅ | H | —SCH₂— | 2-pyridyl | 180 | (HCl) |
| 4 | 6-Cl | 4-CH₃ | H | —SCH₂— | 2-pyridyl | 180 | (HCl) |
| 5 | H | 5-OCH₃ | H | —SCH₂— | 2-pyridyl | 155-95 | (2 · HCl) |
| 6 | H | 5-OH | H | —SCH₂— | 2-pyridyl | 190-200 | (HCl) |
| 7 | H | 5-COCH₃ | H | —SCH₂— | 2-pyridyl | 144 | (base) |

Table I-continued

Compounds of formula I prepared

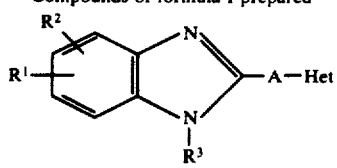

| Ex. | R² | R¹ | R³ | A | Het | M.P. °C | |
|---|---|---|---|---|---|---|---|
| 8 | H | 5-COOH | H | —SCH₂— | 2-pyridyl | 268 | (base) |
| 9 | H | 5-COOC₂H₅ | H | —SCH₂— | 2-pyridyl | 180–90 | (2 · HCl) |
| 10 | H | H | H | —SCH₂— | 2-(6-methylpyridyl) | 121 | (HCl) |
| 11 | H | H | H | —SCH₂— | 2-(6-chloropyridyl) | 145 | (base) |
| 12 | H | H | H | —SCH₂— | (2-(4-chloropyridyl) | | |
| 13 | H | H | H | —SCH₂— | 2-(5-methylpyridyl) | 134 | (HCl) |
| 14 | H | 5-CH₂OH | H | —SCH₂— | 2-pyridyl | | |
| 15 | H | H | H | —S—CH(CH₃)— | 2-pyridyl | 165 | (HCl) |
| 16 | H | H | COCH₃ | —SCH₂— | 2-pyridyl | 119–24 | (base) |
| 17 | H | H | COOCH₃ | —SCH₂— | 2-pyridyl | 78 | (base) |

BIOLOGICAL EFFECT

The compounds of the invention possess worthwhile therapeutic properties as gastric acid affecting compounds.

Thus, a testing technique for compounds having secretory activity were used on the dog. The testing was performed in acute dog experiments with a modified perfusion technique.

The stomach of the anaesthetized dog was provided with one tube through the oesophagus for instillation of fluid and another tube via the ligated pylorus through duodenum for drainage of fluid. Saline was instilled in a volume of 5 ml/kg body weight, and the instillation fluid was changed every 15 minutes.

The samples collected were titrated to pH 7.0 with 0.04 N NaOH using a Radiometer automatic titrator, and the acid output per 15 minutes was calculated (collection periods).

Gastric acid secretion was induced by pentagastrin in 1–2 µg/kg.

Test compounds in 0.5% Methocel suspension were given into the duodenum close to the ligation at least 2 hours following onset of stimulation, when the secretion had reached a steady level for three consecutive 15 minutes periods.

The gastric secretion response was noted, whereby it was found that all compounds of the examples above were gastric acid secretion inhibitors.

In the table below the inhibition of gastric acid secretion obtained in the test above is given for some of the compounds above, whereby the inhibition is expressed as percent inhibition of the pentagastrin induced gastric acid secretion. The amount of active agent administered was 10 mg/kg body weight.

Table

| Compound | Ex. 1 | 3 | 5 | 9 | 16 | 17 |
|---|---|---|---|---|---|---|
| % inhibition 10 mg/kg | 89 | 86 | 40 | 70 | 80 | 76 |

The compounds of Examples 1, 3, and 9 have also been tested with regard to the duration of the effect obtained in conscious dog provided with a ventricel fistula, the gastric acid secretion being induced with pentagastrin. The amount of gastric acid secreted before the administration of active agent was determined using a titrator, whereupon the gastric acid secretion was determined using a titrator after administration. In the table below the inhibition in % of basic secretion has been given for two different dose levels.

Table

| Compound acc. to | Amount adm. | Time | % inhibition | | |
|---|---|---|---|---|---|
| | | | 1 | 2 | 3 hrs |
| Example 1 | 1 mg/kg | | 20 | 25 | 25 |
| 3 | 1 mg/kg | | 20 | 25 | 25 |
| 9 | 1 mg/kg | | 20 | 25 | 25 |
| 1 | 2 mg/kg | | 50 | 60 | 65 |
| 3 | 2 mg/kg | | 50 | 60 | 65 |
| 9 | 2 mg/kg | | 50 | 60 | 65 |

As evident from the table above the inhibition of gastric acid secretion is improved 2 and even 3 hrs after administration.

EXAMPLE 20

A syrup containing 2% (weight per volume) of active substance was prepared from the following ingredients:

| | |
|---|---|
| 2-[2-(pyridylmethyl)thio]-(4-methyl)-benzimidazole · HCl | 2.0 g |
| Sugar | 0.6 g |
| Glycerine | 30.0 g |
| Flavoring agent | 5.0 g |
| Ethanol 96% | 0.1 g |
| Distilled water | 10.0 ml |
| | ad 100.0 ml |

Sugar, saccharine and the ether salt were dissolved in 60 g of warm water. After cooling glycerine and a solution of flavoring agents dissolved in ethanol were added. To the mixture water was then added to 100 ml.

The above given active substance may be replaced with other pharmaceutically acceptable acid addition salts.

EXAMPLE 21

2-[2-pyridylmethylthio]-(5-ethyl)-benzimidazole HCl (250 g) was mixed with lactose (175.8 g), potato starch (169.7 g) and colloidal silicic acid (32 g). The mixture was moistened with 10% solution of gelatine and was granulated through a 12 mesh sieve. After drying potato starch (160 g), talc (50 g) and magnesium stearate (5 g) were admixed and the mixture thus obtained was pressed into tablets (10,000) which contain 25 mg of substance. The tablets are sold on the market provided with a breaking score to give another dose than 25 mg or to give multiples thereof when broken.

EXAMPLES 22

Granules were prepared from 2-[2-pyridyl(methyl)-methylthio]-benzimidazole-p-hydroxybenzoate (250 g), lactose (175.9 g) and an alcoholic solution of polyvinylpyrrolidone (25 g). After the drying step the granules were mixed with talc (25 g) potato starch (40 g) and magnesium stearate (2.50 g) and was pressed into 10,000 biconvex tablets. These tablets are primarily coated with a 10% alcoholic solution of shellac and thereafter with an aqueous solution containing saccharose (45%), gum arabicum (5%), gelatine (4%) and dyestuff (0.2%). Talc powder sugar were used for powdering after the first five coatings. The coating was then coated with a 66% sugar syrup and polished with a 10% carnauba wax solution in carbon tetrachloride.

EXAMPLE 23

2-[2-(4-chloropyridylmethyl)thio]-benzimidazole-hydrochloride (1 g), sodium-chloride (0.8 g) and ascorbic acid (0.1 g) were dissolved in sufficient amount of distilled water to give 100 ml of solution. This solution, which contains 10 mg of active substance on each ml, was used in filling ampoules, which were sterilized by heating at 120° C for 20 minutes.

We claim:

1. A method of inhibiting gastric acid secretion by administering to mammals, including man, suffering from gastric acid secretion disturbances, in an effective amount, a compound of the formula I

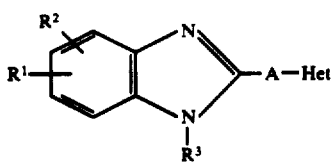

(I)

wherein $R^1$ and $R^2$ are the same or different and are selected from the group consisting of hydrogen, alkyl having up to seven carbon atoms, halogen, nitro, carboxy, carboalkoxy, wherein the alkyl group has up to four carbon atoms, carboalkoxyalkyl wherein each of the two alkyl groups has up to four carbon atoms, hydroxy, alkoxy having up to five carbon atoms, hydroxyalkyl having up to seven carbon atoms, and alkanoyl having up to four carbon atoms, in any position; $R^3$ is selected from the group consisting of hydrogen, alkanoyl having up to four carbon atoms, and carboalkoxy wherein the alkyl group has up to four carbon atoms; A is selected from the group consisting of —SCH$_2$— and —SCH(CH$_3$)—, whereby the S atom is bound to the benzimidazolyl group; and Het is selected from the group consisting of 2-pyridyl and 2-pyridyl substituted with lower alkyl groups such as methyl, ethyl and propyl, and halogen substituents such as chloro and bromo, or its therapeutically acceptable salts.

2. A method according to claim 1, wherein a compound of formula 1, wherein $R^1$ is hydrogen, hydroxy, hydroxymethyl, methyl, ethyl, methoxy, acetyl, carboxy or carbethoxy, $R^2$ is hydrogen, methyl or chloro, $R^3$ is hydrogen, methyl, acetyl, or carbomethoxy, A is —SCH$_2$— and Het is 2-pyridyl, or 2-pyridyl substituted with methyl, chloro, or its therapeutically acceptable salts, is administered.

3. A method according to claim 1, wherein a compound of formula I, wherein $R^1$, $R^2$ and $R^3$ are hydrogen, A is —S—CH(CH$_3$)— and Het is 2-pyridyl, or its therapeutically acceptable salts is administered.

4. A method according to claim 1, wherein
   1. 2-[2-pyridylmethylthio]-(4-methyl)benzimidazole,
   2. 2-[2-pyridylmethylthio]-(4,6-dimethyl)benzimidazole,
   3. 2-[2-pyridylmethylthio]-(5-ethyl)benzimidazole,
   4. 2-[2-pyridylmethylthio]-(4-methyl, 6-chloro)-benzimidazole,
   5. 2-[2-pyridylmethylthio]-(5-methoxy)benzimidazole,
   6. 2-[2-pyridylmethylthio]-(5-hydroxy)benzimidazole,
   7. 2-[2-pyridylmethylthio]-(5-acetyl)benzimidazole,
   8. 2-[2-pyridylmethylthio]-(5-carboxy)benzimidazole,
   9. 2-[2-pyridylmethylthio]-(5-carbethoxy)benzimidazole,
   10. 2-[2-(6-methyl)pyridylmethylthio]-benzimidazole,
   11. 2-[2-(6-chloro)pyridylmethylthio]-benzimidazole,
   12. 2-[2-(4-chloro)pyridylmethylthio]-benzimidazole,
   13. 2-[2-(5-methyl)pyridylmethylthio]-benzimidazole,
   14. 2-[2-pyridylmethylthio]-(5-hydroxymethyl)-benzimidazole,
   15. 2-[2-pyridyl-(methyl)methylthio]-benzimidazole,
   16. 2-[2-pyridylmethylthio]-(N-acetyl)-benzimidazole,
   17. 2-[2-pyridylmethylthio]-(N-methoxycarbonyl)-benzimidazole, or its therapeutically acceptable salts is administered for inhibiting gastric acid secretion.

5. A pharmaceutical composition for inhibiting gastric acid secretion wherein the active ingredient is 2-[2-pyridylmethylthio]-(5-methoxy)benzimidazole or a pharmaceutically acceptable nontoxic addition salt thereof, in a therapeutically effective amount ranging from 0.1% to 95% by weight of the composition in association with a pharmaceutically acceptable carrier.

6. A pharmaceutical composition for inhibiting gastric acid secretion wherein the active ingredient is 2-[2-pyridylmethylthio]-(5-hydroxy)benzimidazole or a pharmaceutically acceptable non-toxic addition salt thereof, in a therapeutically effective amount ranging from 0.1% to 95% to weight of the composition in association with a pharmaceutically acceptable carrier.

7. A pharmaceutical composition for inhibiting gastric acid secretion wherein the active ingredient is 2-[2-pyridylmethylthio]-(5-acetyl)benzimidazole or a pharmaceutically acceptable nontoxic addition salt thereof, in a therapeutically effective amount ranging from 0.1% to 95% by weight of the composition in association with a pharmaceutically acceptable carrier.

8. A pharmaceutical composition for inhibiting gastric acid secretion wherein the active ingredient is 2-[2-pyridylmethylthio]-(5-carboxy)benzimidazole or a pharmaceutically acceptable non-toxic addition salt thereof, in a therapeutically effective amount ranging from 0.1% to 95% by weight of the composition in association with a pharmaceutically acceptable carrier.

9. A pharmaceutical composition for inhibiting gastric acid secretion wherein the active ingredient is 2-[2-pyridylmethylthio]-(5-carbethoxy)benzimidazole or a pharmaceutically acceptable non-toxic addition salt thereof, in a therapeutically effective amount ranging from 0.1% to 95% by weight of the composition in association with a pharmaceutically acceptable carrier.

10. A pharmaceutical composition for inhibiting gastric acid secretion wherein the active ingredient is 2-[2-pyridylmethylthio]-5-hydroxymethyl)-benzimidazole or a pharmaceutically acceptable non-toxic addition salt thereof, in a therpaeutically effective amount ranging from 0.1% to 95% by weight of the composition in association with a pharmaceutically acceptable carrier.

11. A pharmaceutical composition for inhibiting gastric acid secretion wherein the active ingredient is 2-[2-pyridylmethylthio]-(N-acetyl)benzimidazole or a pharmaceutically acceptable non-toxic addition salt thereof, in a therapeutically effective amount ranging from 0.1% to 95% by weight of the composition in association with a pharmaceutically acceptable carrier.

12. A pharmaceutical composition for inhibiting gastric acid secretion wherein the active ingredient is 2-[pyridylmethylthio]-(N-methoxycarbonyl)benzimidazole or a pharmaceutically acceptable non-toxic addition salt thereof, in a therapeutically effective amount ranging from 0.1% to 95% by weight of the composition in association with a pharmaceutically acceptable carrier.

* * * * *